(12) United States Patent
Rousseau et al.

(10) Patent No.: US 8,926,921 B2
(45) Date of Patent: Jan. 6, 2015

(54) ANALYSIS UNIT INTENDED TO BE USED IN ANALYSIS APPARATUS

(75) Inventors: Alain Rousseau, Paris (FR); Olivier Lerat, Agey (FR)

(73) Assignee: Biocode Hycel France SA, Pouilly en Auxois (FR)

( * ) Notice: Subject to any disclaimer, the term of this patent is extended or adjusted under 35 U.S.C. 154(b) by 725 days.

(21) Appl. No.: 12/374,508

(22) PCT Filed: Jul. 19, 2007

(86) PCT No.: PCT/FR2007/001241
§ 371 (c)(1),
(2), (4) Date: Oct. 19, 2009

(87) PCT Pub. No.: WO2008/009821
PCT Pub. Date: Jan. 24, 2008

(65) Prior Publication Data
US 2010/0034700 A1  Feb. 11, 2010

(30) Foreign Application Priority Data

Jul. 21, 2006  (FR) ........................... 06 06685

(51) Int. Cl.
| | | |
|---|---|---|
| *B01L 9/06* | (2006.01) | |
| *B01L 9/00* | (2006.01) | |
| *B65D 71/50* | (2006.01) | |
| *G01N 35/10* | (2006.01) | |
| *G01N 35/00* | (2006.01) | |
| *G01N 35/02* | (2006.01) | |

(52) U.S. Cl.
CPC .. *G01N 35/1002* (2013.01); *G01N 2035/00524* (2013.01); *B65D 71/50* (2013.01); *G01N 35/026* (2013.01)
USPC ........................................... 422/430; 422/50

(58) Field of Classification Search
CPC ..................................... B01L 9/06; B01L 9/00
USPC ....................................................... 422/61, 50
See application file for complete search history.

(56) References Cited

U.S. PATENT DOCUMENTS 4,234,103 A * 11/1980 Strobl et al. ................. 222/83.5
4,350,253 A    9/1982 Rusteberg
(Continued)

FOREIGN PATENT DOCUMENTS

| DE | 19540877 A1 | 5/1997 |
|---|---|---|
| EP | 0790063 A1 | 8/1997 |

(Continued)

OTHER PUBLICATIONS http://www.merriam-webster.com/dictionary/neck, Obtained on Feb. 16, 2012.

*Primary Examiner* — Christine T Mui
(74) *Attorney, Agent, or Firm* — Porzio, Bromberg & Newman, P.C.

(57) ABSTRACT

This analysis package comprises: a cartridge (3) for reactive products comprising several recipients (4) for reactive products arranged one above the other, wherein each recipient comprises a neck (6), wherein the neck of each recipient is provided with a closing device (7) and a plate (13) for receiving the cartridge (3), wherein the plate comprises a receptacle (22) which is open to the top for receiving the bases of the recipients (4) for reactive products which bases form the cartridge; and means for keeping the recipients for reactive products in position situated in distance from the receptacle, wherein the position keeping means are organized such that they cooperate with the necks of the recipients for reactive products when the bases of said recipients are received in the receptacle (22).

17 Claims, 2 Drawing Sheets

(56) References Cited

U.S. PATENT DOCUMENTS

| | | | | | |
|---|---|---|---|---|---|
| 4,970,053 | A | * | 11/1990 | Fechtner | 422/554 |
| 5,075,082 | A | * | 12/1991 | Fechtner | 422/554 |
| 5,186,339 | A | * | 2/1993 | Heissler | 211/74 |
| 5,322,668 | A | | 6/1994 | Tomasso | |
| 5,344,036 | A | * | 9/1994 | Stanescu et al. | 215/251 |
| 5,655,673 | A | * | 8/1997 | Weterrings et al. | 211/75 |
| 6,149,872 | A | * | 11/2000 | Mack et al. | 422/554 |
| 2004/0241864 | A1 | * | 12/2004 | Sattler et al. | 436/43 |
| 2005/0153426 | A1 | * | 7/2005 | Muller et al. | 435/287.1 |

FOREIGN PATENT DOCUMENTS

| | | | |
|---|---|---|---|
| EP | 1583447 | A2 | 11/2004 |
| JP | 542150 | U | 6/1993 |
| JP | 715566 | U | 3/1995 |
| JP | 200467122 | A | 3/2004 |
| JP | 2004163319 | A | 6/2004 |
| WO | 9961919 | A2 | 12/1999 |
| WO | 03020427 | A1 | 3/2003 |
| WO | WO 03020427 A1 * | 3/2003 | ............ B01L 9/00 |

\* cited by examiner

ANALYSIS UNIT INTENDED TO BE USED IN ANALYSIS APPARATUS

CROSS REFERENCE TO RELATED APPLICATION

This is a National Stage of International Application PCT/FR2007/001241, filed 19 Jul. 2007, which claims the benefit of Application No. 0606685, filed in France on 21 Jul. 2006, the disclosures of which Applications are incorporated by reference herein.

BACKGROUND OF THE INVENTION

The present invention concerns an analysis unit intended to be used in analysis apparatus.

DESCRIPTION OF THE PRIOR ART

The document EP 0 871 894 describes a first type of analysis unit. This analysis unit consists of a cartridge for reagents. According to this document, the cartridge comprises several reagent receptacles fixed to each other by means of connecting slides provided on the transverse sides of the receptacles. Each receptacle consists of a body formed by two half-shells obtained by means of plastic injection-molding and ultrasound-welding and a lid ultrasound-welded onto the opening defined by the half-shells. Moreover, each receptacle comprises two slides of matching shape which are molded integrally with the respective half-shells and are provided respectively on each of its transverse sides, each slide being intended to co-operate with a matching slide of an adjacent receptacle.

The manufacture of these receptacles requires the injection-molding of a large number of parts and subsequent ultrasound-welding of these parts. Since injection-molding and ultrasound-welding require very costly tools, the cost of manufacturing the receptacles and therefore the cartridge is very high.

The fact that the receptacles are assembled by means of slides molded integrally with the bodies of the receptacles requires a high degree of precision during molding of the half-shells and therefore requires an injection-molding technique in order to produce the half-shells. Thus, it is not possible to produce these half-shells using another less costly molding technique.

Moreover, the assembly of a large number of parts may result in the risk of leakages of the receptacles and therefore discarding of a certain number of receptacles.

Moreover, in order to identify these possible leakage defects in the receptacles, it is required to provide very costly means on the vessel production line.

As a result the manufacture and assembly of a cartridge such as that described in the document EP 0,871,894 is very complex and costly.

The document EP 1,432,516 describes a second type of analysis unit comprising a reagent cartridge and a carrier intended to receive the cartridge.

According to this document, the cartridge comprises several reagent receptacles made of plastic and assembled together. As in the document EP 0,871,894, each receptacle consists of a body formed by two half-shells obtained by means of plastic injection-molding and ultrasound-welding and a lid ultrasound-welded onto the opening defined by the half-shells.

Thus, as before, the cost of manufacturing these cartridges is very high since the receptacles are obtained by means of injection-molding of a large number of parts and ultrasound-welding of these parts.

The carrier described in the document EP 1,432,516 comprises a seat which is open upwards and intended to receive the base of the reagent receptacles forming the cartridge, as well as means for keeping the receptacles in position. These position keeping means comprise, on the one hand, snap-in grooves provided on the front wall of the carrier and intended to cooperate with matching ribs provided on the longitudinal front sides of the receptacles and, on the other hand, vertical notches provided on the end wall of the carrier and intended to cooperate with vertical hooks provided on the longitudinal rear sides of the receptacles.

The formation of the hooks and the snap-in ribs molded integrally with the body of the receptacles requires a high degree of precision during molding of the half-shells forming the receptacle bodies, resulting in the need for an injection-molding technique in order to produce the half-shells. Thus, it is not possible to produce these half-shells using another less costly molding technique.

As a result, the manufacture of an analysis unit such as that described in the document EP 1,432,516 is very complex and costly.

The present invention aims to overcome these drawbacks.

The technical problem underlying the invention therefore consists in providing an analysis unit which has a simple structure and has a much lower manufacturing cost.

SUMMARY OF THE INVENTION

To this end, the invention concerns an analysis unit intended to be used in an analysis apparatus, characterized in that it comprises:
 a cartridge for reagents comprising several reagent receptacles assembled together, each receptacle comprising a neck, the neck of each receptacle being equipped with a closing device, and
 a carrier intended to receive the cartridge, the carrier comprising a seat which is open upwards and intended to receive the base of the reagent receptacles forming the cartridge, as well as position keeping means for keeping the reagent receptacles in position, situated at a distance from the seat, the position keeping means being arranged so as to cooperate with the necks of the reagent receptacles when the bases of the latter are received inside the seat.

Thus, the receptacles forming the cartridge are kept in position on the carrier of the analysis apparatus by means of co-operation of the neck of each receptacle with the position keeping means provided on the carrier. Consequently, it is not necessary to provide complex position keeping means directly on the receptacles. It is thus possible to simplify manufacture of the receptacles and therefore decrease the cost of manufacture of the cartridge and therefore the analysis unit.

As a result, the cost of manufacture of the receptacles and therefore the cartridge is greatly reduced compared to the cost of manufacturing the cartridges according to the prior art.

According to an embodiment of the invention, the position keeping means comprise several notches provided on the carrier and each intended to cooperate with the neck of a reagent receptacle when its base is received inside the seat.

Advantageously, the distance between the axes of two adjacent necks is a multiple of the distance between two adjacent notches.

Owing to this fact, it is possible to use receptacles with different volumes to form the cartridge, while ensuring that the neck of each receptacle will be situated perfectly opposite the respective notch provided on the carrier when the cartridge is mounted on the latter.

Advantageously, the carrier comprises a substantially vertical end wall, the upper longitudinal edge of which comprises a substantially perpendicular folded flange in which the notches are provided.

Preferably, the folded flange comprises a succession of notches uniformly distributed along its length.

According to another characteristic feature of the invention, the bottom longitudinal edge of the end wall has a substantially perpendicular folded flange comprising a rim substantially parallel to the end wall, the rim and the end wall forming together with the folded flange the seat intended to receive the base of the reagent receptacles.

Advantageously, the carrier has a stirring system comprising a tubular support with a vertical axis mounted in a rotationally movable manner on the carrier and having on its external surface rotational driving means.

Preferably, the rotational driving means comprise a toothed wheel intended to be rotationally driven by a driving mechanism of an analysis apparatus.

According to one embodiment of the invention, each receptacle is made of plastic and as one piece, the neck of each receptacle being blow-molded integrally with the body of the respective receptacle.

Thus, each receptacle of the cartridge is made directly as one piece by means of plastic blow-molding.

Owing to this fact, it is not necessary to provide very costly injection-molding means and ultrasound-welding means.

According to another embodiment of the invention, each receptacle comprises two substantially parallel longitudinal sides intended to co-operate with the carrier and two transverse sides with a matching shape, the transverse sides of two adjacent receptacles directed towards each other resting against each other.

Advantageously, the cartridge comprises receptacles with different volumes. It is thus possible to perform analyses requiring the use of different reagents in different quantities.

According to a characteristic feature of the invention, the receptacles are fixed together by means of a self-adhesive strip surrounding the latter.

Thus, it is not necessary to provide complex and costly mechanical means for performing assembly of the different receptacles. It is thus possible to reduce even further the cost of manufacturing the cartridge.

Preferably, the self-adhesive strip forms a label which has on its external surface information about the cartridge, in particular a description of the reagents used and the analysis to be performed, the information being provided, for example, in the form of a bar code.

According to another characteristic feature of the invention, the closing device of each receptacle is formed by a cap, the skirt of which has, on its inner side, means for fixing by means of screwing or snap-engagement onto the neck of the receptacle and the bottom of which, which is at least partially open, is equipped with a piercible membrane.

According to another characteristic feature of the invention, the analysis unit comprises a tubular container mounted inside the tubular support, the axis of the tubular container being offset with respect to the axis of the tubular support.

Owing to this offset arrangement of the axis of the tubular container and the axis of the tubular support, it is possible to perform orbital stirring of the solution contained inside the container when the toothed support wheel is rotationally driven by the driving mechanism of the analysis apparatus. Thus, when the solution contains magnetic particles intended to capture the analyte which is to be analyzed, this orbital movement of the container prevents agglomeration of the magnetic particles against the internal surface of the latter.

Since these magnetic particles are denser than water, they tend to form a deposit inside the container. In this respect it is very important that these magnetic particles should remain suspended in the solution during analysis.

As a result, before performing an analysis, the operator removes the container from the tubular support, shakes it and then repositions it inside the tubular support. This operation of ensuring that the magnetic particles are suspended is simpler than the operations performed with the cartridges described in the documents EP 1,432,516 and EP 0,871,894. In fact, according to these documents, the container forms an integral part of the cartridge, which means that the entire cartridge must be shaken to ensure that the magnetic particles contained inside the container remain suspended.

Moreover, in contrast to that described in the documents EP 1,432,516 and EP 0,871,894, the means for rotationally driving the container are not provided directly on the container which is disposable, but on the tubular support. This minimizes the cost of manufacture of the container and therefore of the analysis unit.

Preferably, the inner wall of the container has longitudinal fins. This helps improve stirring of the magnetic particles when the container is rotationally driven.

Advantageously, the outer wall of the container has a longitudinal groove intended to co-operate with a matching rib provided on the inner wall of the tubular support so as to ensure fixing of the container in the support.

In any case, the invention will be understood more fully with the aid of the following description, with reference to the accompanying schematic drawing showing, by way of a non-limiting example, an embodiment of this cartridge.

DESCRIPTION OF THE PREFERRED EMBODIMENTS

Figure 1:
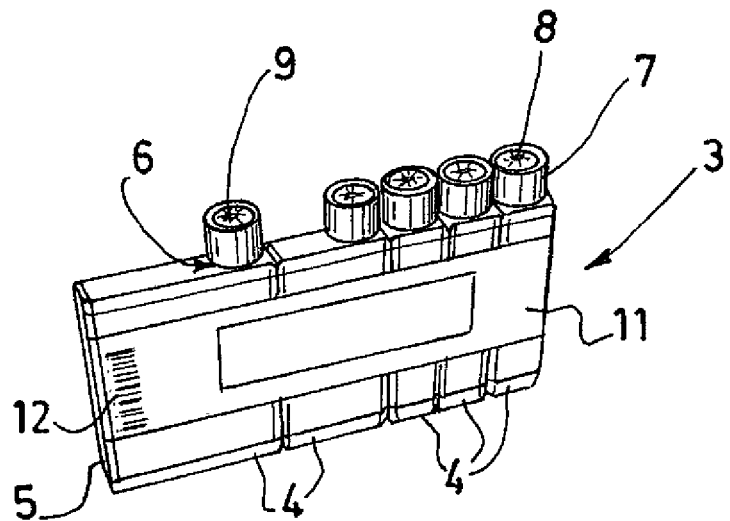
FIG. 1 is a perspective view of a cartridge according to the invention.

As shown more particularly in FIG. 1, the analysis unit 2 comprises a cartridge 3 for reagents, comprising five reagent receptacles 4 each containing a liquid reagent.

Each receptacle 4 is made of plastic as one piece and comprises a body 5 and a neck 6 formed integrally by means of blow-molding. The body 5 of each receptacle has a general rectangular shape viewed in section and comprises two substantially parallel longitudinal sides intended to co-operate with an analysis apparatus carrier and two transverse sides with a matching shape. The transverse sides of two adjacent receptacles directed towards each other rest against each other.

It must be noted that the neck 6 of each receptacle is equipped with a closing device 7 and is intended to cooperate with a notch with a matching shape provided on the analysis carrier. The closing device of each receptacle is formed by a cap 7, the skirt of which has, on its inner side, means for fixing by means of screwing or snap-engagement onto the neck of the receptacle and the bottom of which, which is at least partially open, is equipped with a piercible membrane 8. The piercible membrane comprises several slits 9 allowing easy insertion or retraction of a probe or a needle of the analysis apparatus inside the receptacle.

These different receptacles 4 are fixed to each other by means of a self-adhesive label 11 surrounding the latter. The self-adhesive label 11 has, on its outer side, a bar code 12 containing information about the cartridge, in particular for example a description of the reagents used and the analysis to be performed.

The cartridge 3 comprises three identical 10 ml receptacles as well as a 20 ml receptacle and another 40 ml receptacle. In this case, the analysis to be performed therefore requires the use of five different reagents in different quantities for determining the presence of a precise substance in a sample to be analyzed.

However, taking into account the different nature of the analyses which can be performed by the analysis apparatus, the number, the size and the position of the receptacles used may vary.

Figure 2:
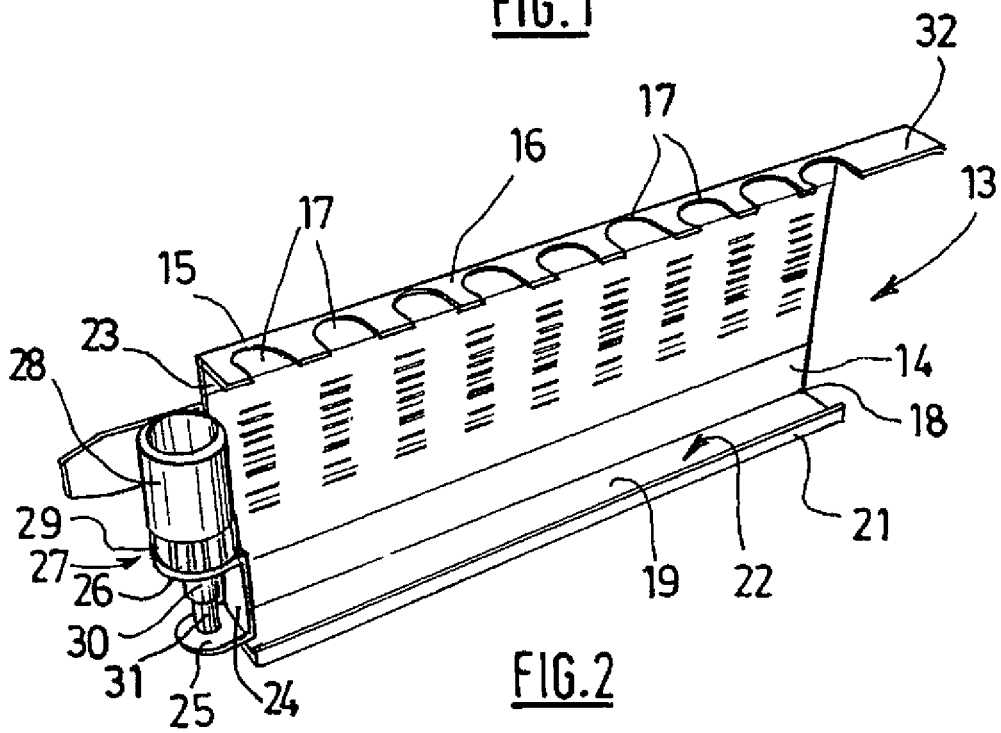
FIG. 2 is a perspective view of a carrier according to the invention.
Figure 3:
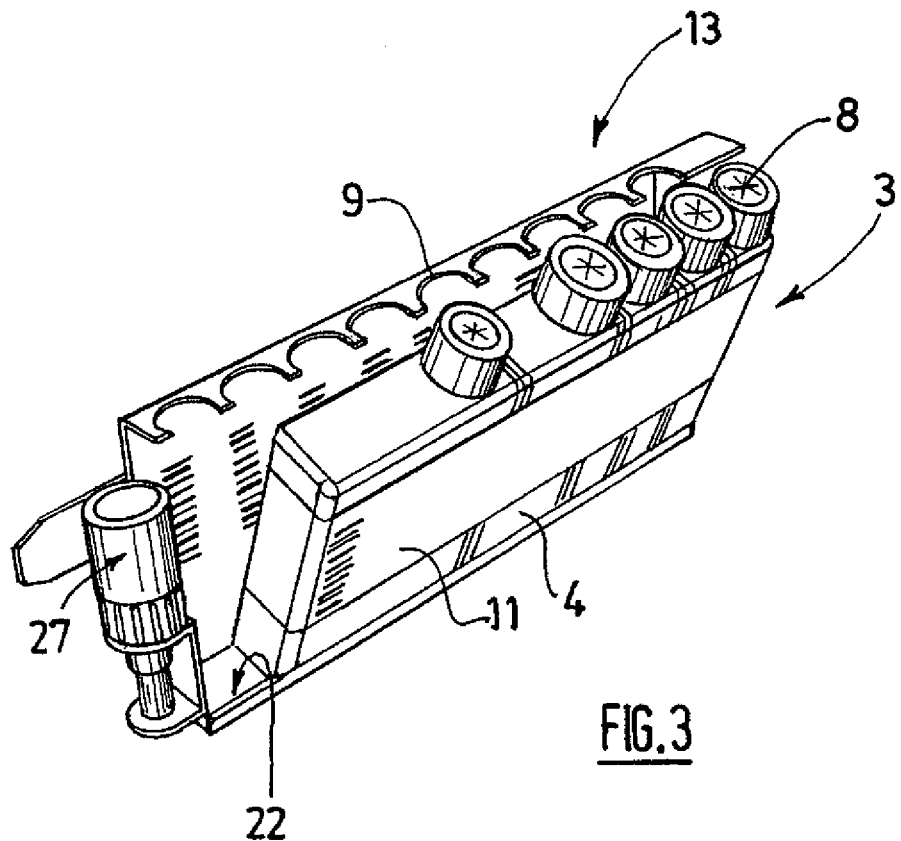
FIG. 3 is a perspective view of an analysis unit according to the invention during assembly.

As shown more particularly in FIG. 2, the analysis unit 2 also comprises a carrier 13 made of plastic. The carrier 13 has a substantially vertical end wall 14, the upper longitudinal edge 15 of which has a longitudinal folded flange 16 extending substantially perpendicularly with respect to the end wall and over the entire length of the latter. The folded flange 16 comprises nine notches 17 which are uniformly spaced along its length, each notch 17 being intended to cooperate with the neck of a reagent receptacle of the cartridge.

The bottom transverse edge 18 of the end wall has a longitudinal folded flange 19 extending substantially perpendicularly with respect to the end wall 14 and over the entire length of the latter. The folded flange 19 comprises a rim 21 substantially parallel to the end wall 14 and extending over the entire length of the latter.

The rim 21 and the end wall 14 form together with the folded flange 16 a seat 22 which is open upwards and intended to receive the base of at least one reagent receptacle.

It should be noted that the first and second folded flanges form the top wall and bottom walls of the carrier, respectively.

The transverse edge 23 of the end wall directed towards the analysis apparatus comprises a transverse folded flange 24 extending substantially perpendicularly with respect to the end wall and over a portion of this transverse edge. It should be noted that the three folded flanges have substantially the same width.

The folded flange 24 has a lower lug 25 and an upper lug 26 extending outwards perpendicularly with respect to the latter. Each lug comprises a circular through-orifice, the two orifices being coaxial.

The carrier 13 also has a stirring system comprising a tubular support 27 mounted in a rotationally movable manner on the folded flange 24. The tubular support has a cylindrical body 28 which has on its outer surface a toothed wheel 29 intended to be rotationally driven by a driving mechanism of an analysis apparatus. The cylindrical body 28 is prolonged in succession by a first cylindrical portion 30 and a second cylindrical portion 31 with a smaller diameter, the two cylindrical portions being coaxial with the cylindrical body 27. The first cylindrical portion 30 is engaged inside the orifice of the upper lug 26 while the second cylindrical portion 31 is engaged inside the orifice of the lower lug 25.

It should be noted that the second cylindrical portion 31 comprises, at its free end, a catch cooperating with the bottom side of the lower lug 25 so as to prevent displacement of the tubular support relative to the carrier.

The carrier also has a handle 32 integral with the folded flange 16 allowing insertion and removal of the cartridge of the analysis device.

In order to fix the cartridge 3 on the carrier 13, it is sufficient to engage firstly the base of each receptacle inside the seat 22 of the carrier, and then engage the neck of each receptacle inside the respective notch 17. It should be noted that the notches extend in a plan substantially perpendicular to the axis of the necks of the receptacles when the latter are fixed on the carrier.

In order to ensure proper fixing of the receptacles on the carrier, the space between the upper side of each receptacle and the bottom side of the closing cap 7 corresponds substantially to the thickness of the folded flange 16, and the shape of each notch 17 matches that of the neck of each receptacle. Moreover, proper fixing of the receptacles on the carrier is also achieved owing to the fact that the space between the bottom folded flange 19 and the top folded flange 16 corresponds substantially to the height of the receptacles 4.

It should be noted that the notches 17 also prevent lateral movement of the receptacles with respect to the carrier 13.

Figure 4:
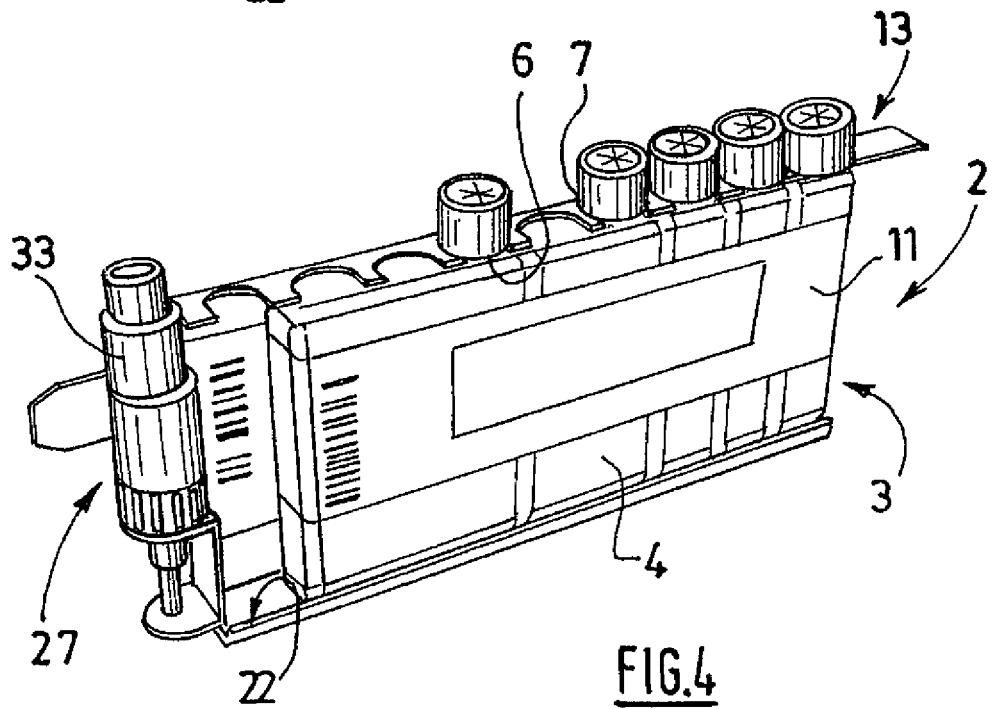
FIG. 4 is a perspective view of an analysis unit according to the invention, in the assembled condition.

As shown in FIG. 4, the analysis unit also comprises a tubular container 33 which is removably mounted in the tubular support 27, the axis of the tubular container being offset with respect to the axis of the tubular support. Advantageously, the tubular container has longitudinal fins provided on its inner wall and holds a solution containing magnetic particles intended to capture the analyte which is to be analyzed.

It should be noted that the outer wall of the container has a longitudinal groove cooperating with a matching rib provided on the inner wall of the tubular support in order to ensure fixing of the container in the support.

As goes without saying, the invention is not limited to the sole embodiment of this cartridge, described above by way of example, and instead embraces all the variations of embodiment. Thus, in particular, the number of notches and/or receptacles could be different. Moreover, the carrier 13 could be metallic, for example made of stainless steel, which would improve the thermal and electrical conductivity for detection of the level of the reagents in the receptacles.

The invention claimed is:

1. An analysis unit configured to be used in an analysis apparatus, comprising:
   a cartridge for reagents comprising several reagent receptacles assembled together, each reagent receptacle comprising a body and a neck, the neck of each reagent receptacle being equipped with a closing device, and
   a carrier configured to receive the cartridge, the carrier comprising:
   a seat which is open upwards and configured to receive the base of the reagent receptacles forming the cartridge, and
   several notches situated at a distance from the seat, the distance between the notches and the seat corresponding to at least the height of the bodies of the reagent receptacles, each notch has a shape corresponding at least partially to the shape of the neck of the respective reagent receptacle, the neck of each reagent receptacle is configured to engage inside the respective notch, each of said notches cooperates with the neck of a reagent receptacle when the base of the latter is received in the seat, the notches extending in a plane perpendicular to axis of the necks of the reagent receptacles.

2. The analysis unit as claimed in claim 1, wherein the distance between the axes of two adjacent necks is a multiple of the distance between two adjacent notches.

3. The analysis unit as claimed in claim 1, wherein the carrier comprises a vertical end wall, an upper longitudinal edge of which comprises a perpendicular folded flange in which the notches are provided.

4. The analysis unit as claimed in claim 3, wherein the folded flange comprises a succession of notches which are uniformly distributed along its length.

5. The analysis unit as claimed in claim 3, wherein a bottom longitudinal edge of the end wall has a perpendicular folded flange comprising a rim parallel to the end wall, the rim and the end wall forming together with the folded flange the seat intended to receive the base of the reagent receptacles.

6. The analysis unit as claimed in claim 1, wherein the carrier has a stirring system comprising a tubular support with a vertical axis mounted in a rotationally movable manner on the carrier and having on its outer surface rotational driving means.

7. The analysis unit as claimed in claim 6, wherein the rotational driving means comprise a toothed wheel intended to be rotationally driven by a driving mechanism of an analysis apparatus.

8. The analysis unit as claimed in claim 1, wherein each receptacle is made of plastic and as one piece, the neck of each receptacle being blow-molded integrally with the body of the respective receptacle.

9. The analysis unit as claimed in claim 1, wherein each receptacle comprises two parallel longitudinal sides intended to cooperate with the carrier and two transverse sides with a matching shape, the transverse sides of two adjacent receptacles directed towards each other resting against each other.

10. The analysis unit as claimed in claim 1, wherein the cartridge has receptacles with different volumes.

11. The analysis unit as claimed in claim 1, wherein the receptacles are fixed to each other by means of a self-adhesive strip surrounding the receptacles.

12. The analysis unit as claimed in claim 11, wherein the self-adhesive strip forms a label containing on its outer side information about the cartridge, in particular a description of the reagents used and the analysis to be performed, the information being provided for example in the form of a bar code.

13. The analysis unit as claimed in claim 1, wherein the closing device of each receptacle is formed by a cap, the skirt of which has, on its inner side, means for fixing by means of screwing or snap-engagement onto the neck of the receptacle and the bottom of which, which is at least partially open, is equipped with a pierceable membrane.

14. The analysis unit as claimed in claim 6, further comprising a tubular container mounted in the tubular support, the axis of the tubular container being offset with respect to the axis of the tubular support.

15. The analysis unit as claimed in claim 14, wherein the inner wall of the container has longitudinal fins.

16. The analysis unit as claimed in claim 15, wherein the outer wall of the container has a longitudinal groove intended to cooperate with a matching rib provided on the inner wall of the tubular support in order to ensure fixing of the container in the support.

17. An analysis unit configured to be used in an analysis apparatus, comprising:
   a cartridge for reagents comprising several reagent receptacles assembled together, each reagent receptacle comprising a body and a neck, the neck of each reagent receptacle being equipped with a closing device, and
   a carrier configured to receive the cartridge, the carrier comprising:
   a seat which is open upwards and configured to receive the base of the reagent receptacles forming the cartridge,
   a vertical end wall having an upper longitudinal edge comprising a perpendicular folded flange, the folded flange being situated at a distance from the seat, the distance between the folded flange and the seat corresponding to at least the height of the bodies of the reagent receptacles, and
   several notches provided on the folded flange, each notch has a shape corresponding at least partially to the shape of the neck of the respective reagent receptacle, the neck of each reagent receptacle is configured to engage inside the respective notch, each of said notches being intended to cooperate with the neck of a reagent receptacle when the base of the latter is received in the seat.

* * * * *